(12) United States Patent
Young et al.

(10) Patent No.: US 9,358,557 B2
(45) Date of Patent: Jun. 7, 2016

(54) LIQUID DIFFUSER

(71) Applicant: Young Living Essential Oils, LC, Lehi, UT (US)

(72) Inventors: D. Gary Young, Alpine, UT (US); James T. Davis, II, Springville, UT (US); Son Q. Le, Highland, UT (US)

(73) Assignee: Young Living Essential Oils, LC, Lehi, UT (US)

( * ) Notice: Subject to any disclaimer, the term of this patent is extended or adjusted under 35 U.S.C. 154(b) by 46 days.

(21) Appl. No.: 14/137,835

(22) Filed: Dec. 20, 2013

(65) Prior Publication Data
US 2015/0174595 A1    Jun. 25, 2015

(51) Int. Cl.
| B05B 7/00 | (2006.01) |
| B05B 7/24 | (2006.01) |
| A61L 9/14 | (2006.01) |
| B05B 1/26 | (2006.01) |
| B05B 15/04 | (2006.01) |

(52) U.S. Cl.
CPC ............. B05B 7/0012 (2013.01); A61L 9/14 (2013.01); B05B 7/2429 (2013.01); B05B 1/262 (2013.01); B05B 15/0406 (2013.01)

(58) Field of Classification Search
CPC .... B05B 7/0483; B05B 7/0869; B05B 7/064; B05B 7/265; B05B 7/30; B05B 7/0012; B05B 7/2429; B05B 15/0406; B05B 1/262; A61L 9/14
USPC ........................................................ 239/340
See application file for complete search history.

(56) References Cited

U.S. PATENT DOCUMENTS

| 912,106 | A | * | 2/1909 | Frazier | ................. | B05B 7/2472 |
| | | | | | | 239/305 |
| 1,243,514 | A | * | 10/1917 | Hamlin | ................. | B05B 7/2472 |
| | | | | | | 239/305 |
| 1,652,422 | A | * | 12/1927 | Ascherl | ................. | B05B 7/2429 |
| | | | | | | 222/144 |
| 2,052,869 | A | * | 9/1936 | Coanda | ................. | D02G 1/161 |
| | | | | | | 131/211 |

(Continued)

FOREIGN PATENT DOCUMENTS

EP        1829560        9/2007

OTHER PUBLICATIONS

"Carburetor", Wikipedia, downloaded Dec. 20, 2013, pp. 13, http://en.wikipedia.org/wiki/carburetor.

(Continued)

*Primary Examiner* — Duane Smith
*Assistant Examiner* — Stephen Hobson
(74) *Attorney, Agent, or Firm* — Kunzler Law Group, PC (57) ABSTRACT

The disclosure relates to a diffuser apparatus and system. The diffuser apparatus includes a gas supply line with an injection port facing a first direction for emitting a gas stream into a diffuser space. The diffuser apparatus further includes a dome-shaped surface positioned a first distance away from the injection port. The dome-shaped surface is in downstream fluid communication with the gas stream. The diffuser apparatus further includes a liquid feed line that is connectable in fluid receiving communication with a liquid source. The liquid feed line includes a suction port disposed on the dome-shaped surface facing a second direction. During operation of the apparatus, passing the gas stream over the suction port suctions a particle stream through the liquid feed line in order to form a combination stream.

15 Claims, 7 Drawing Sheets

(56) References Cited

U.S. PATENT DOCUMENTS

| | | | | | |
|---|---|---|---|---|---|
| 2,553,159 | A * | 5/1951 | Able | ............... | B05B 7/2421 239/308 |
| 3,084,870 | A * | 4/1963 | Hagadorn | ............ | B05B 7/2421 221/106 |
| 3,085,752 | A * | 4/1963 | Drell | ............... | B05B 7/2421 239/303 |
| 3,107,058 | A * | 10/1963 | Corbett | ............ | G01N 1/2813 239/346 |
| 3,180,578 | A * | 4/1965 | Hagadorn | ............ | B05B 7/2421 222/132 |
| 3,454,228 | A * | 7/1969 | Mossop | ............ | B05B 7/2421 222/635 |
| 3,591,088 | A * | 7/1971 | Green | ............... | B65D 83/685 222/635 |
| 3,770,209 | A * | 11/1973 | Wilcox | ............ | B05B 7/0483 239/434 |
| 4,222,525 | A * | 9/1980 | Hildebrandt | ......... | B05B 7/2427 222/401 |
| 4,606,501 | A * | 8/1986 | Bate | ............... | B05B 7/2429 239/346 |
| 4,681,262 | A * | 7/1987 | Sprute | ............... | B05B 7/2416 239/306 |
| 4,963,228 | A * | 10/1990 | Steen | ............... | D21F 1/026 162/336 |
| 5,186,395 | A * | 2/1993 | Brody | ............... | B05B 11/3077 222/255 |
| 5,255,852 | A * | 10/1993 | Morrison | ............ | B05B 7/2429 239/346 |
| 5,292,244 | A * | 3/1994 | Xiong | ............... | B01F 5/0451 239/414 |
| 5,346,135 | A * | 9/1994 | Vincent | ............ | B05B 7/2472 239/306 |
| 5,513,982 | A * | 5/1996 | Althaus | ............ | B01F 5/0451 431/182 |
| 5,518,311 | A * | 5/1996 | Althaus | ............ | B01F 5/0451 138/37 |
| 5,658,358 | A * | 8/1997 | Chyou | ............... | B01F 5/0473 138/37 |
| 5,860,598 | A * | 1/1999 | Cruz | ............... | B05B 7/0075 239/346 |
| 6,203,186 | B1 * | 3/2001 | Cruz | ............... | B01F 3/04049 239/425 |
| 6,341,736 | B1 * | 1/2002 | Liao | ............... | B05B 7/2429 239/306 |
| 6,405,944 | B1 * | 6/2002 | Benalikhoudja | ........ | A61L 9/145 128/200.18 |
| 6,568,604 | B1 * | 5/2003 | Behan | ............... | A61L 9/12 239/305 |
| D520,129 | S | 5/2006 | Sevy | | |
| D526,710 | S | 8/2006 | Sevy | | |
| 7,104,471 | B1 * | 9/2006 | Behan | ............... | B05B 7/0012 239/311 |
| 7,152,813 | B2 * | 12/2006 | Chen | ............... | B05B 7/2429 239/302 |
| 7,407,118 | B2 | 8/2008 | Sevy | | |
| 7,878,418 | B2 | 2/2011 | Sevy | | |
| 7,913,933 | B2 * | 3/2011 | Van Roemburg | ..... | B05B 7/0012 239/338 |
| D645,947 | S | 9/2011 | Sevy | | |
| 8,789,769 | B2 * | 7/2014 | Fenton | ............... | A62C 31/02 239/422 |
| 8,840,038 | B2 * | 9/2014 | Lehr | ............... | B05B 7/2424 222/633 |
| 8,944,671 | B2 * | 2/2015 | Son | ............... | B01F 3/0873 239/418 |
| 9,211,357 | B1 * | 12/2015 | Li | ............... | A61L 9/14 |
| 2003/0209613 | A1 * | 11/2003 | Miyauchi | ............ | B05B 7/02 239/418 |
| 2005/0077383 | A1 * | 4/2005 | Sevy | ............... | B05B 1/28 239/290 |
| 2006/0283985 | A1 * | 12/2006 | Ikeuchi | ............ | B05B 1/26 239/543 |
| 2009/0095823 | A1 * | 4/2009 | Gardega | ............ | B01F 3/02 239/419.3 |
| 2010/0081020 | A1 * | 4/2010 | Lee | ............... | B01F 5/0413 429/411 |
| 2010/0084484 | A1 * | 4/2010 | Sevy | ............... | A61M 11/06 239/4 |
| 2013/0140380 | A1 * | 6/2013 | Pelfrey | ............ | A47K 5/14 239/311 |

OTHER PUBLICATIONS

U.S. Appl. No. 29/478,588, YL41, Notice of Allowance, Sep. 12, 2014.

* cited by examiner

LIQUID DIFFUSER

FIELD

This disclosure relates to liquid diffuser systems.

BACKGROUND

Diffusing liquids into the air has a variety of benefits. For example, inhalation of certain liquids may improve a user's respiratory health or may efficiently introduce medication into the bloodstream through the lungs. In another example, liquids can be diffused into the air as a pleasant fragrance or to mask the smell of odorous compounds. Various devices exist for diffusing liquid into the air. For example, nebulizers, diffusers, and atomizers can deliver liquid particles to the air for inhalation.

SUMMARY

The subject matter of the present application has been developed in response to the present state of the art, and in particular, in response to the problems and needs in the art of liquid diffusers.

A diffuser apparatus is presented. The diffuser apparatus may include a gas supply line that is connectable in gas receiving communication with a pressurized gas source. The gas supply line may include an injection port facing a first direction for operably emitting a gas stream into a diffuser space in the first direction. The diffuser apparatus may further include a dome-shaped surface positioned a first distance away from the injection port. The dome-shaped surface may be in downstream fluid communication with the gas stream. The diffuser apparatus further may include a liquid feed line that is connectable in fluid receiving communication with a liquid source. The liquid feed line may include a suction port disposed on the dome-shaped surface facing a second direction. In one embodiment, the first direction and the second direction are not parallel to each other. During operation of the apparatus, passing the gas stream over the suction port suctions a particle stream through the liquid feed line in order to form a combination stream (e.g., a mixture of the gas stream and the particle stream).

In one implementation, the suction port is disposed on a crest portion of the dome-shaped surface and the gas stream is directed at a base portion of the dome-shaped surface. Further, the injection port may have a certain diameter and a second distance between the dome-shaped surface and another element opposite the dome-shaped surface may be greater than the certain diameter of the injection port. In one example, the diffuser space is a diffuser chamber and the dome-shaped surface is a protrusion on a first wall of the diffuser chamber. Further, the diffuser chamber may have a second wall, opposite the first wall, that is displaced a second distance from the first wall so as to not substantially increase the operable velocity of the gas stream across the dome-shaped surface. In other words, the injection port may have a certain diameter and the diffuser chamber may have a second wall of the diffuser chamber, opposite the first wall, that is displaced a second distance from the first wall so that the second distance is greater than the certain diameter. Further, in one embodiment the first direction is substantially perpendicular to the second direction.

Another diffuser apparatus is presented. The diffuser apparatus may include a removable component that is detachably engagable with a base. The removable component may include a liquid source, such as a liquid vial that can be replaced. The diffuser apparatus may further include a diffuser chamber that is integrated with one or the other or both of the base and the removable component. The diffuser chamber may include an injection port that is facing a first direction and that is in fluid receiving communication with a pressurized gas channel of the base. The injection port may operably emit a gas stream into the diffuser chamber in the first direction. The diffuser chamber may further include a dome-shaped surface protruding from a first wall of the diffuser chamber. The dome-shaped surface, according to one embodiment, is positioned a first distance away from the injection port in downstream fluid communication with the gas stream. Still further, the diffuser apparatus may include a suction port that is facing a second direction and that is disposed on the dome-shaped surface. The suction port may be in fluid receiving communication with the liquid source and operably passing the gas stream over the suction port may suction a particle stream from the liquid source into the diffuser chamber to form a combination stream.

According to one embodiment, the diffuser chamber may have a second wall, opposite the first wall, that is displaced a second distance from the first wall so as to not substantially increase the operable velocity of the gas stream across the dome-shaped surface. In other words, the injection port may have a certain diameter and the diffuser chamber may have a second wall, opposite the first wall, that is displaced a second distance from the first wall so that the second distance is greater than the certain diameter. In one embodiment, the liquid source is a liquid vial coupled to the removable component and at least a portion of the diffuser chamber is positioned above and open to at least a portion of the liquid vial.

During operation of the diffuser apparatus, the combination stream may contact a third wall of the diffuser chamber in order to separate a heavy fraction from a light fraction. In other words, the heavy fraction of the combination stream falls into the liquid vial and the light fraction of the combination stream passes through the vent. The apparatus may further include a securing mechanism for securing together the base and the removable component. Also, the liquid source may include a liquid vial containing essential oils. According to one implementation, the liquid vial is detachably coupled to the removable component so that the liquid vial can be replaced. The base may include a pressurized gas source in fluid providing communication with the pressurized gas channel. In one embodiment, the pressurized gas source may be an air compressor. Further, the apparatus may include a controller integrated with the base for controlling the dynamics of the gas stream. Also, the diffuser apparatus may include a user interface for regulating the controller.

A diffuser system is also presented. The diffuser system may include a base that has an air compressor in fluid providing communication with a pressurized gas channel. The diffuser system may further include a removable component detachably engaged with the base. The removable component may also be detachably coupled to a liquid vial containing essential oil. The diffuser system may further include a diffuser chamber integrated with the removable component. The diffuser chamber may include an injection port facing a first direction and in fluid receiving communication with the pressurized gas channel of the base. The injection port, according to one embodiment, operably emits a gas stream into the diffuser chamber in the first direction. The diffuser chamber may further include a dome-shaped surface protruding from a first wall of the diffuser chamber. The dome-shaped surface may be positioned at a first distance away from the injection port in downstream fluid communication with the gas stream. The gas stream, according to one implementation, is directed at a base portion of the dome-shaped surface. The diffuser chamber may also include a suction port facing a second direction and disposed on a crest portion of the dome-shaped surface. The suction port may be in fluid receiving communication with the liquid vial and operably passing the gas stream over the suction port may cause a particle stream from the liquid vial to be drawn up into the diffuser chamber in order to form a combination stream. The diffuser chamber may also include a vent for operably venting at least a fraction of the combination stream.

Reference throughout this specification to features, advantages, or similar language does not imply that all of the features and advantages that may be realized with the present disclosure should be or are in any single embodiment of the invention. Rather, language referring to the features and advantages is understood to mean that a specific feature, advantage, or characteristic described in connection with an embodiment is included in at least one embodiment of the subject matter disclosed herein. Thus, discussion of the features and advantages, and similar language, throughout this specification may, but do not necessarily, refer to the same embodiment.

Furthermore, the described features, advantages, and characteristics of the disclosure may be combined in any suitable manner in one or more embodiments. One skilled in the relevant art will recognize that the subject matter of the present application may be practiced without one or more of the specific features or advantages of a particular embodiment. In other instances, additional features and advantages may be recognized in certain embodiments that may not be present in all embodiments of the disclosure. Further, in some instances, well-known structures, materials, or operations are not shown or described in detail to avoid obscuring aspects of the subject matter of the present disclosure. These features and advantages of the present disclosure will become more fully apparent from the following description and appended claims, or may be learned by the practice of the disclosure as set forth hereinafter.

BRIEF DESCRIPTION OF THE DRAWINGS

In order that the advantages of the disclosure will be readily understood, a more particular description of the disclosure briefly described above will be rendered by reference to specific embodiments that are illustrated in the appended drawings. Understanding that these drawings depict only typical embodiments of the disclosure and are not therefore to be considered to be limiting of its scope, the subject matter of the present application will be described and explained with additional specificity and detail through the use of the accompanying drawings, in which:

FIG. 1A is a cross-sectional side view of a diffuser apparatus, according to one embodiment;

FIG. 1B is a cross-sectional side view of the diffuser apparatus of FIG. 1A but with pressure variations depicted, according to one embodiment;

FIG. 2A is a cross-sectional side view of a diffuser apparatus, according to one embodiment;

FIG. 2B is a cross-sectional side view of a diffuser apparatus, according to one embodiment;

FIG. 2C is a cross-sectional side view of a diffuser apparatus, according to one embodiment;

FIG. 2D is a cross-sectional side view of a diffuser apparatus, according to one embodiment;

FIG. 3 is a perspective view of a diffuser system, according to one embodiment;

FIG. 4 is a perspective-exploded view of the diffuser system of FIG. 3, according to one embodiment;

FIG. 5 is a perspective-exploded view of the diffuser system of FIG. 4 but with a section cut-away to show a cross-sectional view, according to one embodiment;

FIG. 6 is a cross-sectional side view of a diffuser system, according to one embodiment; and FIG. 7 is a magnified cross-sectional side view of the diffuser system of FIG. 6, according to one embodiment.

DETAILED DESCRIPTION

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

FIG. 1A is a cross-sectional side view of a diffuser apparatus 100, according to one embodiment. The diffuser apparatus 100 includes a gas supply line 10, a dome-shaped surface 120, and a liquid supply line 30. The gas supply line 10 is connectable with a pressurized gas source 50, which is described below in greater detail with reference to FIG. 5. The gas supply line 10 delivers a gas stream 118 to a diffuser space 119 via an injection port 110. The injection port 110 is an opening, orifice, or nozzle that emits the gas stream 118 into the diffuser space 119. The injection port 110 faces a first direction 112 and the gas stream 118 flows in the first direction 112, at least initially upon leaving the injection port 110. In some embodiments, the injection port 110 also has a certain diameter 114 that will be described below in relation to the dimensions of the diffuser space 119. In other embodiments, the injection portion 110 is non-circular and has a certain maximum span of the opening, which can include a maximum length of a rectangular opening, or the like.

As stated, the diffuser apparatus 100 also includes a dome-shaped surface 120. The dome-shaped surface includes a rounded three-dimensional protruding structure. The dome-shaped surface 120 is positioned a first distance 121 away from the injection port 110. The dome-shaped surface 120 is also in downstream fluid communication with the gas stream 118. In other words, the gas stream 118 passes over the dome-shaped surface 120. The diffuser apparatus 100 further includes a liquid supply line 30 that is connectable with a liquid source 60 and that terminates at an open suction port 130. The liquid source 60 is described below in greater detail with reference to FIG. 4. The suction port 130 is disposed on the dome-shaped surface 120 and faces a second direction 132.

FIGS. 2A-D show various embodiments of the relative configurations and orientations of the injection port 110, the dome-shaped surface 120, and the suction port 130. Thus, additional details regarding these components 110, 120, 130 are included below. Specifically, FIGS. 2A-D include details relating to the first distance 121 that separates the injection port 110 and the dome-shaped surface 120 and also includes details relating to the angle between the first direction 112 and the second direction 132. Additionally, details regarding the position of the suction port 130 on the dome-shaped surface 120 are included below with reference to FIG. 1B.

Generally, the diffuser apparatus 100 suctions a particle stream 134 through the suction port 130 and the liquid supply line 30 from the liquid source 60. The suction required to pull the particle stream 134 from the liquid source 60 is generated by the gas stream 118 passing over the suction port 130. The particle stream 134 is a fluid stream of suctioned liquid particles. In one embodiment, the particle stream 134 is a suspension or a dispersion of liquid particles. In another embodiment, depending on the suction pressure and the volatility of the liquid 60, the particle stream 134 may include evaporated liquid particles. According to Bernoulli's principle of fluid dynamics, which is described below in greater detail with reference to FIG. 1B, when a fluid increases in velocity, the pressure of that fluid decreases. Thus, as the gas stream 118 passes over the dome-shaped surface 120, the velocity of the gas stream 118 increases. The increased velocity of the gas stream 118 causes the pressure of the gas stream 118 to drop and creates a low pressure pocket near the suction port 130, thus drawing up the particle stream 134 through the liquid supply line 30. Once the suctioned particle stream 134 joins with the gas stream 118, a combination stream 136 is formed. The combination stream 136 is a nebulized mixture of liquid particles suspended in the gas stream 118.

Figure 1A:
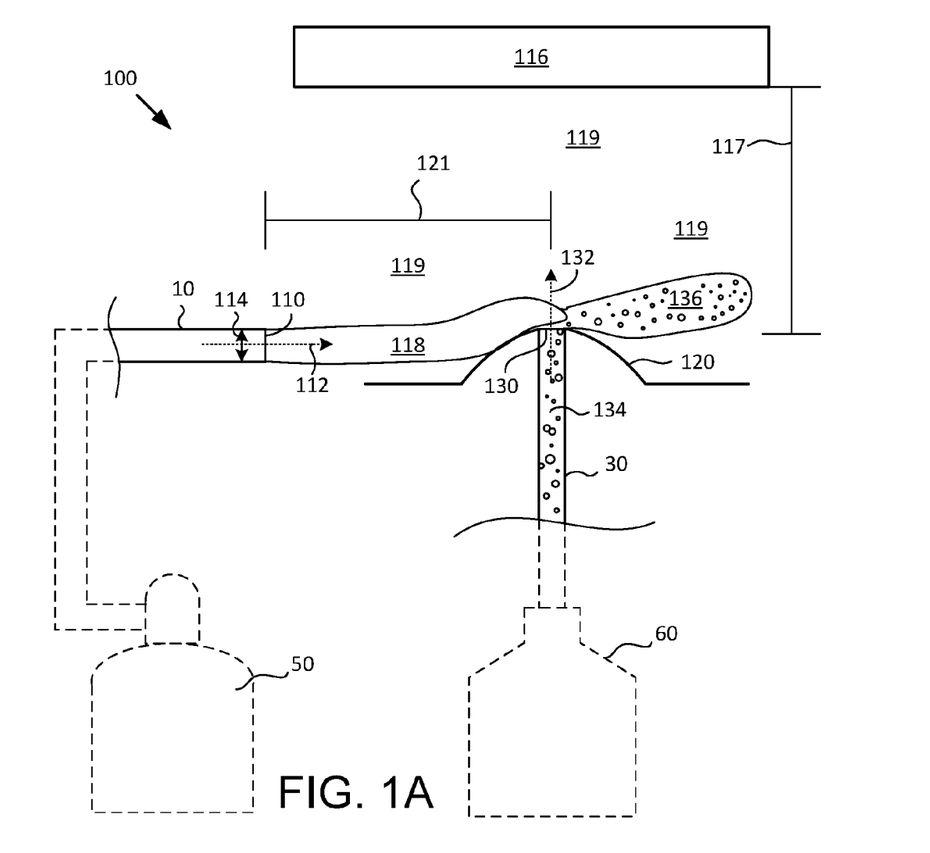

Once again, additional details relating to Bernoulli's principle of fluid dynamics are included below with reference to FIG. 1B. The small circles of various sizes depicted in the flow paths of FIG. 1A represent the liquid particles suctioned up from the liquid source 60. However, the depiction of the particle stream 134 and the combination stream 136 as having a plurality of small circles is not intended as an actual physical representation of the size, dimension, and concentration of the liquid particles. Rather, the small circles are included to represent suspended nature of the liquid particles. However, depending on the magnitude of the vacuum created at the suction port and the volatility of the liquid, in certain embodiments the liquid particles may actually evaporate, thus creating vapor molecules of the originally liquid matter. In such embodiments, the vapor molecules are substantially evenly dispersed with the gas stream 118 and the combination stream 136 would comprise suspended liquid particles.

In one embodiment of the diffuser apparatus 100, the dome-shaped surface 120 is the only element causing the velocity of the gas stream 118 to increase. Certain conventional nebulizers implement a nozzle or orifice that physically restricts the cross-sectional flow area, thus causing the fluid to increase in velocity as it passes through the narrowed section. However, in one embodiment, the diffuser apparatus 100 of the present disclosure does not have an element 116 in the diffuser space 119 opposite the dome-shaped surface 120 that substantially affects the velocity of the gas stream 118. In other words, even if there is an element 116 (i.e., a wall of a chamber, a separate component, etc.) opposite the dome-shaped surface 120, the distance, referred to as the 'second distance' 117 throughout the present disclosure, between the element 116 and the dome-shaped surface 120 is large enough so that the element 116 has no practical/substantial effect on the velocity of the gas stream 118. In other words, the second distance 117 is greater than the certain diameter 114 of the injection port 110 so that no narrowing venturi-type effect occurs.

Figure 1B:
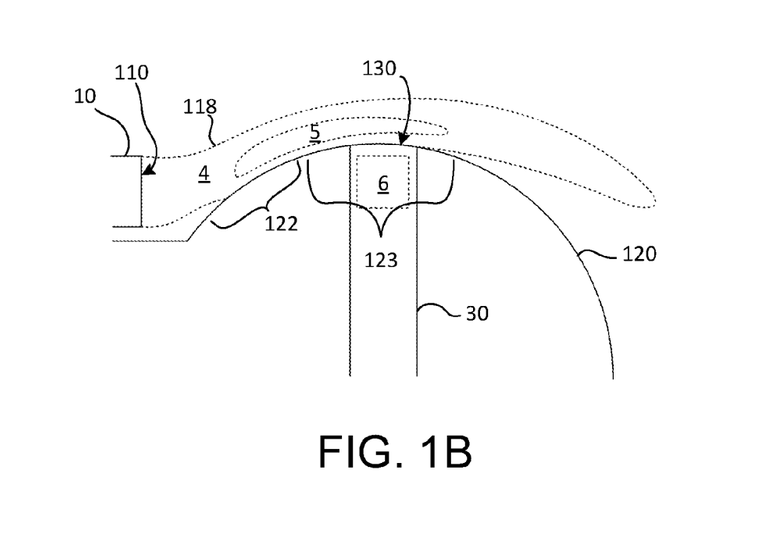

FIG. 1B is a cross-sectional side view of the diffuser apparatus 100 of FIG. 1A but with regions 4, 5, 6 depicted, according to one embodiment. FIG. 1B depicts the gas supply line 10 terminating at the open injection port 110. FIG. 1B also depicts the liquid supply line 30 terminating at the open suction port 130 positioned on the surface of the dome-shaped surface 120. In one embodiment, the dome-shaped surface 120 may have two portions: a base portion 122 that includes the lower, wider section of the dome-shaped surface 120 and a crest portion 123 that includes the top, pinnacle section of the dome-shaped surface 120. In one implementation, the gas stream 118 emitted from the injection port 110 is directed at the base portion 122 of the dome-shaped surface 120 and the suction port 130 is positioned on the crest portion 123 of the dome-shaped surface 120.

The dome-shaped surface 120, according to one embodiment, is a 360 degree rounded dome that is has the appearance of a hemi-sphere. In another embodiment, the dome-shaped surface 120 may be an elliptical dome. For example, the height of the dome-shaped surface 120 may be larger than the width of the dome-shaped surface 120. In yet another embodiment, the dome-shaped surface 120 may only be a portion of a dome. For example, the dome-shaped surface 120 may appear as a bridge-like structure with an arcuate path extending in the first direction 112 across the top portion (crest portion) of the dome with the lateral sides removed. As shown, the dome-shaped surface can have a circular base. In other embodiments, the dome-shaped surface has a non-circular base, such as an oval, ellipse, rectangle, square (as used in a polygonal dome), or the like. In some instances, the dome-shaped surface approximates the shape of a half of a sphere. In other instances, the dome-shaped surface can have a higher or lower pitch than a half a sphere shape. The dome-shaped surface may also have other shapes and configurations, including but not limited to the shape of a corbel dome, a geodesic dome, an onion dome, an oval dome, a parabolic dome, a saucer dome, an umbrella dome, or the like. Accordingly, the dome-shaped surface 120 is defined in the present disclosure as an arcuate protruding surface that causes the velocity of a fluid flowing over the arcuate path and in the direction of the arcuate path to increase.

In FIG. 1B, the gas stream 118 is depicted as having three separate regions or sections 4, 5, 6. These regions 4, 5, 6 represent locations along the flow path of the fluids that have specific flow characteristics. The dimensions and relative sizes of the depicted regions 4, 5, 6 are not intended to exactly represent the changes in the flow characteristics of the gas stream 118. Also, the regions 4, 5, 6 do not represent quantized, discrete, uniform flow characteristic areas but instead generally represent the relative flow characteristic differences at various positions along the flow path.

The first region 4 substantially includes the fluid flow upon initially exiting the injection port 110 and the fluid flow after passing over the dome-shaped surface 120. The second region 5 includes the fluid flow near the crest portion 123 of the dome-shaped surface 120 and the third region 6 includes the fluid flow within the suction port 130. Regardless of the composition of the fluid flow (gas stream 118, particle stream 134, combination stream 136), the regions 4, 5, 6 generally show the different flow conditions at the various locations. For example, the second region 5 has a comparatively higher velocity than the first region 4, thus causing the second region 5 to have a comparatively lower pressure. The third region 6, due to Bernoulli's principle of fluid dynamics, also represents a low pressure region where the particle stream 134 is drawn up from the liquid source 60.

As briefly described above, Bernoulli's principle of fluid dynamics essentially states that, at any point along a fluid flow path, the sum of a kinetic energy factor, a potential energy factor, and pressure energy factor is constant. In other words, ignoring the negligible potential energy factor for the purposes of this disclosure, the sum of the kinetic energy and the pressure energy at a first point in a flow path is the same as the sum of the kinetic energy and the pressure energy at a second point in the flow path. Thus, an increase in the velocity of the gas stream 118 across the dome-shaped surface 120 results in a decrease in pressure across the dome-shaped surface 120. The increased velocity of the gas stream 118 across the dome-shaped surface 120 is caused, in part, by the Coanda effect. The Coanda effect is the tendency of a flowing fluid to be attracted to a nearby surface. Thus, as the gas stream 118 flows out of the injection port 110 and contacts the curved surface of the dome-shaped surface 120, instead of deflecting away from dome-shaped surface 120 the gas stream 118 'bends' to conform to the shape of the dome. Since the flow path over a curved surface is longer than a straight flow path, the velocity of the gas stream 118 increases, thus triggering the vacuum at the suction port 130. It is also contemplated that other principles of fluid dynamics may potentially affect the vacuum created at the suction port 130.

Thus, depending on the flow characteristics of the gas stream 118 and the pressure in the third region 6, the particle stream 134 may either comprise nebulized liquid particles that are suspended in the gas stream 118 to form the combination stream 136 or the particle stream 134 may comprise liquid particles that have evaporated in order to form a combination stream 136 that comprises a mixture of two vapors (two fluids in the gas phase), as briefly described above.

FIGS. 2A-2D are cross-sectional side views of a diffuser apparatus 100, according to one embodiment. The depicted embodiments include a gas supply line 10 and an injection port 110 that has a certain diameter 114. The injection port 110 faces a first direction 112 and, according to one embodiment, is directed at the base portion 122 (not labeled) of the dome-shaped surface 120. The liquid supply line 30 includes an open suction port 130 positioned at a crest portion 123 (not labeled) of the dome-shaped surface 120. Also, the suction port 130 is facing a second direction 132. As described briefly above, the distance (referred to as the first distance 121 throughout the disclosure) between the injection port 110 and the dome-shaped surface 120 may be of various lengths depending on the specifics of a given application. Additionally, the relative angle between the first and second directions 112, 132 may be different depending on the specifics of a given application. In other words, although FIGS. 2A-2D depict multiple representative embodiments, it is anticipated that the configuration and the orientation of the various components is not limited to the depicted embodiments and that one of ordinary skill in the art will recognize related configurations and orientations that fall within the scope of the present disclosure.

Figure 2A:
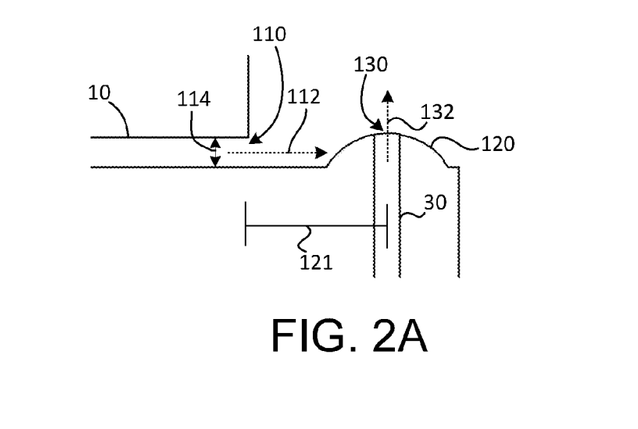
Figure 2B:
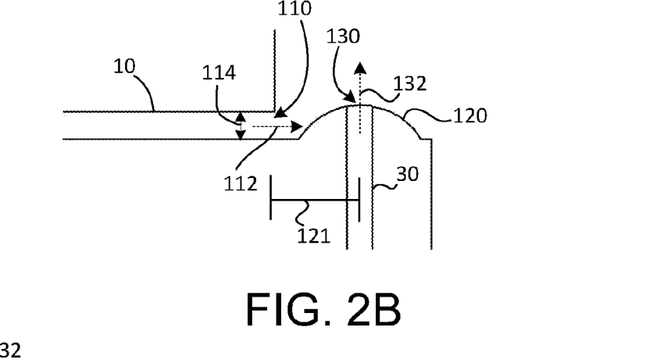
Figure 2C:
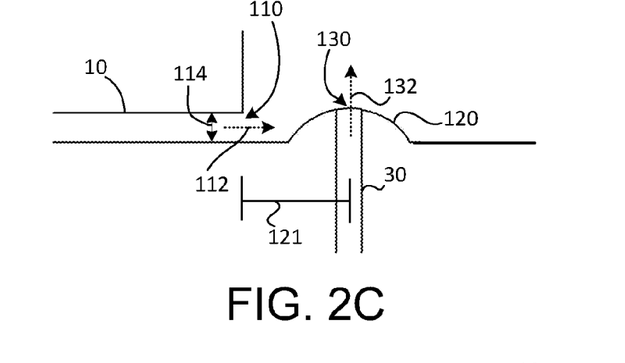
Figure 2D:
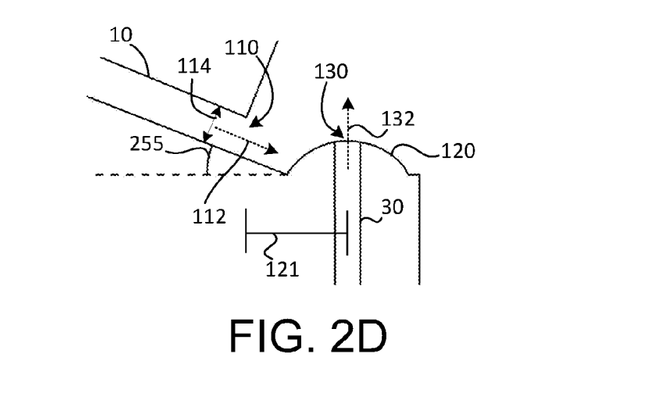

In FIG. 2A the first distance 121, according to one embodiment, is the standard distance that will be used to compare and contrast the other lengths depicted in FIGS. 2B-D. The first distance 121 depicted in FIG. 2B is comparatively shorter than the standard first distance 121 in FIG. 2A. The first distance 121 in FIG. 2C is slightly larger than the first distance 121 from FIG. 2B but is slightly shorter than the standard first distance 121 shown in FIG. 2A. FIG. 2C also shows a surface extending beyond the dome-shaped surface 120 instead of a precipice or a drop-off as depicted in FIGS. 2A, 2C-D. While FIG. 2A-C shows a substantially 90 degree angle between the first direction 112 and the second direction 132, FIG. 2D shows a different angle 255. FIG. 2D shows one embodiment of how the injection port 110 may face a direction 112 that is not perpendicular to the second direction 132. Depending on the specifics of a given application and depending on the desired flow characteristics of the gas stream 118, the gas stream 118 may have different approach angles 255 with respect to the second direction 132. However, in order for the diffuser apparatus 100 to create the desired suction, the first direction 112 and the second direction 132 are not parallel to each other and at least a portion of the gas stream 118 should be directed towards the base portion 122 of the dome-shaped surface 120. In some embodiments, the approach angle 255 may be varied by changing the direction 132 relative to the dome-shaped surface 120 such that the fluid supply line 30 exits the domed shape surface at another angle and/or at a location other than at the base portion 122 of the dome-shaped surface 120.

Figure 3:
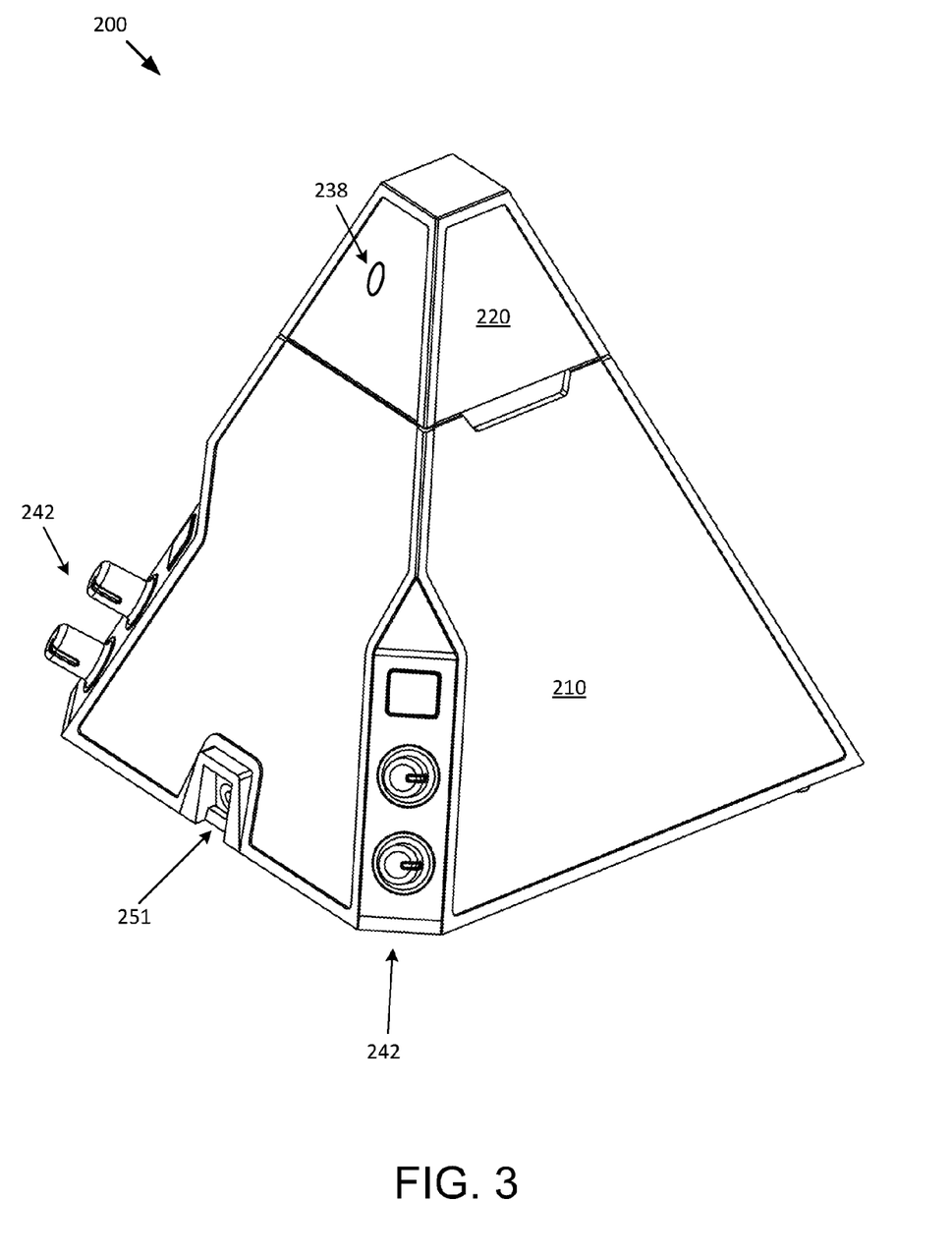

The diffuser apparatus 100 may be combined with various other components, as described below, to form a diffuser system that facilitates the diffusion/dispersion of a liquid into the atmosphere. The diffuser system may be implemented as a fragrance deployment mechanism, an inhalant atomizer, or a nebulizer (among others). FIG. 3 is a perspective view of a diffuser system 200, according to one embodiment. The depicted diffuser system 200 includes a base 210, a removable component 220 detachably engaged with the base 210, a vent 238 for releasing a nebulized liquid into the atmosphere (combination stream 136), a user interface 242 for controlling the operation of the system 200, and a power adapter 251. In one embodiment, the power adapter 251 may be configured to receive alternating current. In another embodiment, the power adapter 251 may be configured to receive direct current. In yet another embodiment, the system 200 may instead operate using battery power and the power adapter 251 may be integrated internally within the base 210 to harness power from a battery assembly.

As described below in greater detail, the base 210 may have a shape and appearance that differs from the embodiment depicted in FIG. 3. For example, the base 210 may be cylindrical or rectangular. Generally the base 210 establishes the support structure from which the combination stream 136 emanates. Also, the base 210 may house various components, such as a source of pressurized gas 50. Although described in greater detail below, the base 210, instead of housing the actual source of the pressurized gas 50, may house a pressurized gas channel 52 that is connectable with an external pressurized gas source 50. Generally, the removable component 220 includes a replaceable liquid source 60. As described below, the liquid source 60 may be detachably coupled with the removable component 220, thus allowing a user to disengage the removable component 220 from the base (e.g., in order to replace the liquid source 60).

The user interface 242 may include various controls for controlling the operation of the system 200. In one embodiment, as depicted, the user interface 242 may include various knobs and/or physical buttons which can be physically maneuvered to adjust the operating settings of the diffuser system 200. In another embodiment, the user interface may also include a digital display showing a user what settings have been selected. In yet another embodiment, the user interface may include an interactive touch-screen. Further, it is anticipated that the system 200 may be controlled via a remote user interface. For example, the diffuser system 200 may be configured to connect with a computer network. Thus, a user may control the system 200 by accessing an application on an electronic device, such as a computer, laptop, tablet, or smartphone.

The user interface 242 may control various aspects of the operation of the system 200. For example, the user interface 242 may control the on-off function of the system 200, the run time of the system 200, and/or a duty cycle (on-off cycle times) of the system 200, and/or on and off times of a duty cycle. In another example, the user interface 242 may control the volume of output produced by the system 200 (e.g., by indirectly controlling the flow of air from the pressurized gas source 50, via the controller 240). In another example, the user interface 242 can control a light, color of the light, and/or light sleep timer that turns the light off after a selected time period. In still another example, the user interface 242 can control music produced by a music player (not shown) of the system 200.

Figure 4:
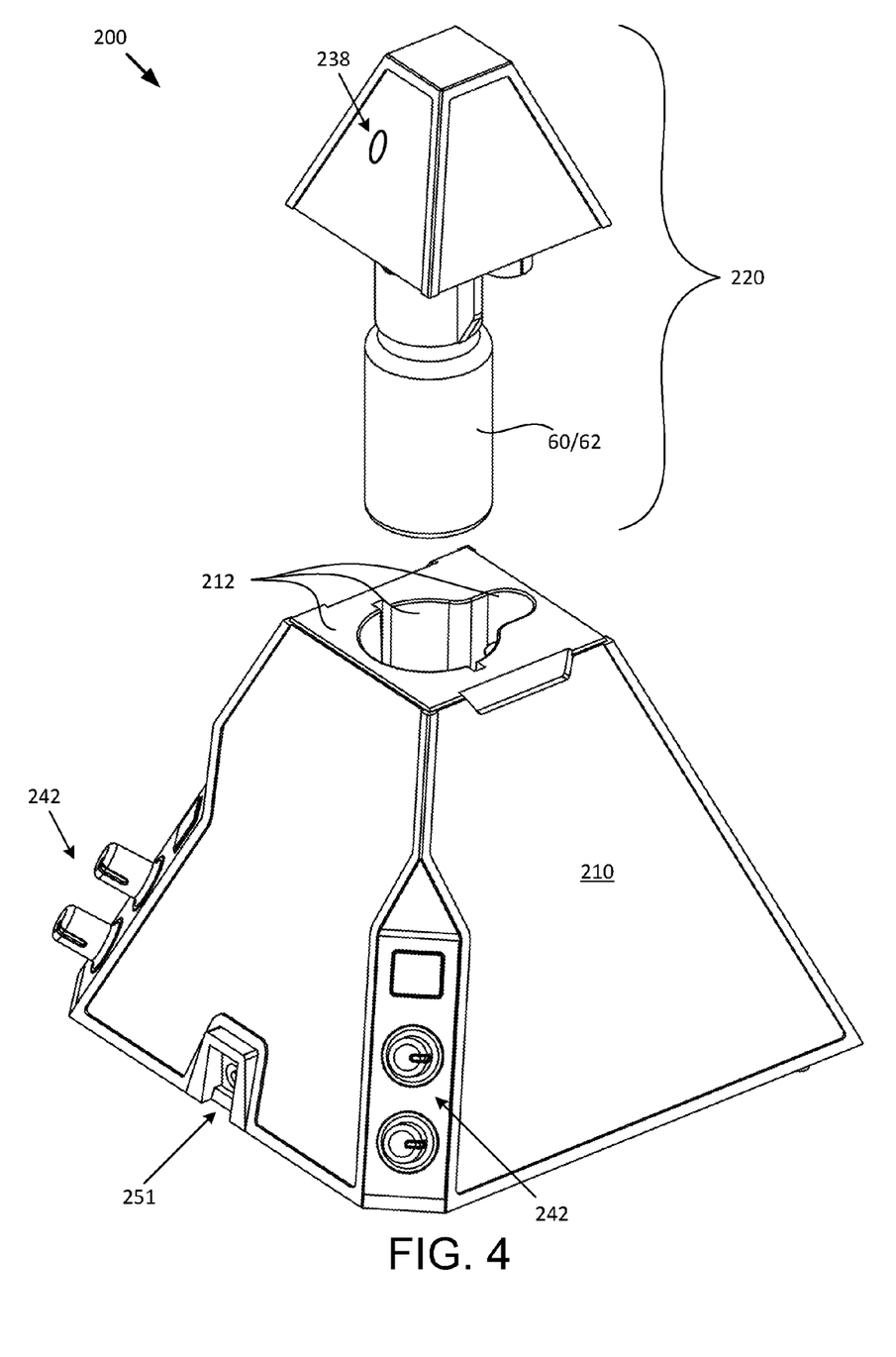

FIG. 4 is a perspective-exploded view of the diffuser system 200 of FIG. 3, according to one embodiment. In the depicted embodiment, the removable component 220 is shown removed (i.e., in a disengaged position) from the base 210. The removable component 220 may comprise a removable, top portion of the body of the diffuser system 200. The removable component 220 can include all or a portion of the diffuser chamber 230 and can be selectively and/or removably coupled to a liquid source 60. Thus, the liquid source 60 may be conveniently accessed, installed, removed, and replaced by merely lifting the removable component 220 off of base 210. A user may thus conveniently change the liquid source to vary the type of liquid (e.g., a fragrance, essential oil, etc.) that is diffused by the diffuser system 200.

As shown, the configuration of the body diffuser system 200, with a base 210 and removable component 220 provides a convenient an aesthetically pleasing structure for diffusing liquids. Specifically, the diffuser system 200 permits the entire liquid source 60 (e.g., a vial or bottle) to be maintained within the body of the diffuser system 200 during storage and operation. This may hide the liquid source that may appear bulky, dirty, or unsightly and simplify the look, feel, and overall appearance of the diffuser system 200. Additionally, the diffuser system 200 conveniently enables a user to access the liquid source 60 by simply lifting upward on the removable component 220 to remove it from the base 210. In some embodiments, the removable component 220 separates from the base 210 with an upward force, and does not required any twisting, torqueing, unlatching, or other separate movement from the user.

The liquid source 60 may be a liquid vial 62 that holds a specific liquid or liquid mixture to be diffused. For example, the liquid source 60 may be a liquid vial 62 containing an essential oil mixture. The essential oil liquid may be one or more essential oils, including a blend of two or more essential oils. In some embodiments, the composition consists essentially of essential oils. In other embodiments, the composition consists solely of essential oils. The essential oils can be substantially pure and uncut essential oils. Essential oils are naturally occurring aromatic liquids found in the roots, stems, bark, seeds, flowers, and other parts of plants. These oils are fat soluble, non-water-based phytochemicals that include volatile organic compounds. The chemistry of any particular essential oil can be very complex and may consist of hundreds of different and unique chemical compounds. In nature, these oils give plants their distinctive smells, provide protection against disease, and assist in pollination. When separated from their parent plant, essential oils in their pure form are translucent with colors ranging from clear to pink or blue.

Suitable essential oils that can be contained within the container, in accordance with some embodiments, include, but not limited to, essential oils from one or more of the following plants (and related plant species): ajowan, almond, allspice, aloe, ammi visnaga (khella), amyris, angelica, anise, apricot, arnica, avocado, copaiba, balsam, basil, bay laurel, benzoin, bergamot, bergaptene, birch, borage, boronia, buchu, cajeput, calalmus, calendula, camellia, cannabis, caraway, cardamom, carnation, carrot, cassia, castor, catnip, cedar, cedarwood, celery, chamomile (including blue chamomile, German chamomile, Moroccan chamomile, Moroccan wild chamomile, and Roman chamomile), champaca, cilantro, cinnamon, cistus, citronella, ciste, clary sage, clementine, clove, cocoa, coconut, combava petitgrain, coriander, cornmint, costus, cumin, cypress, davana, dill, dill weed, elemi, erideron (fleabane), eucalyptus, fennel, sweet fennel, fenugreek, fir, frankincense, galbanum, garlic, genet, geranium, ginger, ginsing, grapefruit, pink grapefruit, white grapefruit, grapeseed, hazelnut, helichrysum, hemp, honeysuckle, hyssop, immortelle, fragrant aster inula, Jamaican gold, jasmine, grandiflorum jasmine, jojoba, jobquille, juniper, lanolin, lantana camara, laurel nobilis, lavender, lemon, lemongrass, lime, litsea, litsea cubeba, lotus, macadamia, mace, mandarin, manuka, marigold, marjarom, massoia, melissa, mimosa, monarda, mugwort, musk, myrrh, myrtle, narcissus, neroli, niaouli, nutmeg, oakmoss, ocotea, olibanum, opopanax, orange, blood orange, sweet orange, oregano, orris, osmanthus, palm, palmarosa, paprika, parsley, patchouli, peanut, pecan, pennyroyal, pepper, black pepper, peppermint, petitgrain, white pine, pine, primrose, ravensara anisata, redberry, rose, rosehip, rosemary, rosewood, rue, sage, sandalwood, seabuckthorn, sesame, shea, spikenard, spruce, blue spruce, St. John's wort, styrax, tagetes, tangerine, tea tree, thuja, thyme, tuberose, valerian, vanilla, verbena, vetiver, violete, vitex, walnut, wintergreen, wormwood, yarrow, and ylang ylang.

Also depicted in FIG. 4 is a plurality of engagement surfaces 212. The engagement surfaces 212 may provide proper alignment of the removable component 220 with the base 210. For example, the engagement surfaces 212 may include a pattern of grooves or notches that only permit the removable component 220 to be engaged on the base 210 in a certain configuration. Additionally, the engagement surfaces 212 may support an inserted liquid vial 62.

A portion of the plurality of engagement surfaces define a cavity 214 shaped and sized to receive a second gas coupling mechanism 216. The second gas coupling mechanism 216 is configured to selectively connect with the pressurized gas line 52 of the pressurized gas source 50 (via a first gas coupling mechanism 253) to the gas supply line 10, as described below with reference to FIG. 6.

Figure 5:
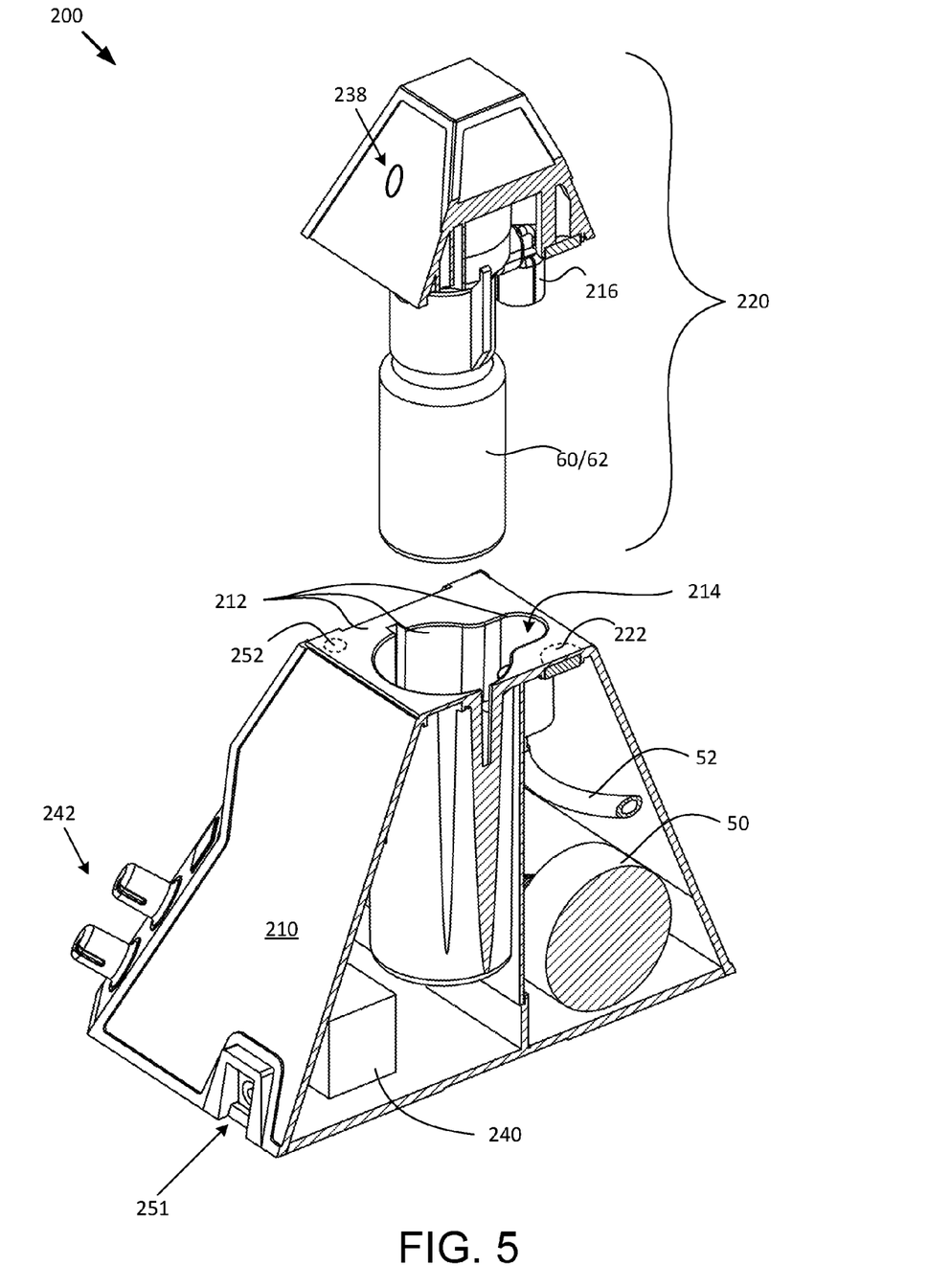

FIG. 5 is a perspective-exploded view of the diffuser system 200 of FIG. 4 but with a section cut-away to show a cross-sectional view, according to one embodiment. As shown, the base 210 may include a pressurized gas channel 52 and a pressurized gas source 50. In one embodiment, the pressurized gas source may be an air compressor or a motor coupled with an air compressor. In such embodiments, the base 210 may include an inlet screen (not depicted) to allow air to enter the compressor. In certain embodiments, the pressurized gas source 50 may be external to the base 210 and the pressurized gas channel 52 may be connectable with the pressurized gas source 50.

Also depicted in FIG. 5 is a controller 240. As described above, a user interface 242 may allow a user to regulate the operation of the system 200 via the controller. For example, the controller may include a logic circuit or computer chip that receives the input from a user via the user interface 242 and executes commands to the various components of the system 200. For example, the controller 240 may be in electrical communication with the pressurized gas source 50. Accordingly, the controller 240 may control the pressure of the gas, the flow rate of the gas (via valves not depicted), the duty cycle of the air compressor, and the time period over which the system 200 should operate.

The diffuser system 200 may further include a securing mechanism 222 that facilitates the engagement between the 
removable component 220 and the base 210. For example, the securing mechanism 222 may include magnets that hold the removable component 220 in place. For example, as shown the removable component 220 can include a separate magnet 223 that is attracted to magnet of the securing mechanism 222 to hold the removable component 220 in place. Furthermore, multiple magnet pairs may be disposed between the removable component 220 and the base 210 to selectively secure the removable component 220 to the base 210. In another embodiment, the securing mechanism 222 may include a latch, a fastener, a bolt, a clasp, a tie, a strap, a pin, or a clip, among others. In other words, the securing mechanism 222 provides a degree of secure engagement between the removable component 220 and the base 210 (e.g., preventing accidental disengagement). The depiction of the securing mechanism 222 as a circular shape on the horizontal surface of the base 210 is only illustrative of one embodiment. Thus, it is contemplated that the securing mechanism 222 may, as described above, be configured in other orientations and still fall within the scope of the present disclosure. Additionally, in one embodiment the removable component 220 may not be entirely detachable from the base 210, but instead may be coupled to the base 210 via a hinge assembly or a sliding track assembly, thus allowing a user to rotate, slide, or swivel the removable component 220 into a 'disengaged position' in order to replace the liquid source 60.

In some embodiments, the diffuser system 200 include an engagement sensor 252 that detects when the removable component 220 is securely or properly engaged with the base 210. The engagement sensor 252 and the securing mechanism 222 may be in electrical communication with the controller 240 and the controller may include a condition that the engagement sensor 252 and/or the securing mechanism 222 are properly configured before commencing a diffuser operation. In some embodiments, the diffuser system may include one or more sensors (not shown) configured to detect when the liquid source 60 is empty. Such sensors may include one or more moisture sensors, weight sensors, or other suitable sensor(s). Furthermore, the controller, 240 may be configured to stop diffusing operations when the one or more sensors determine that the liquid source 60 is empty.

Figure 6:
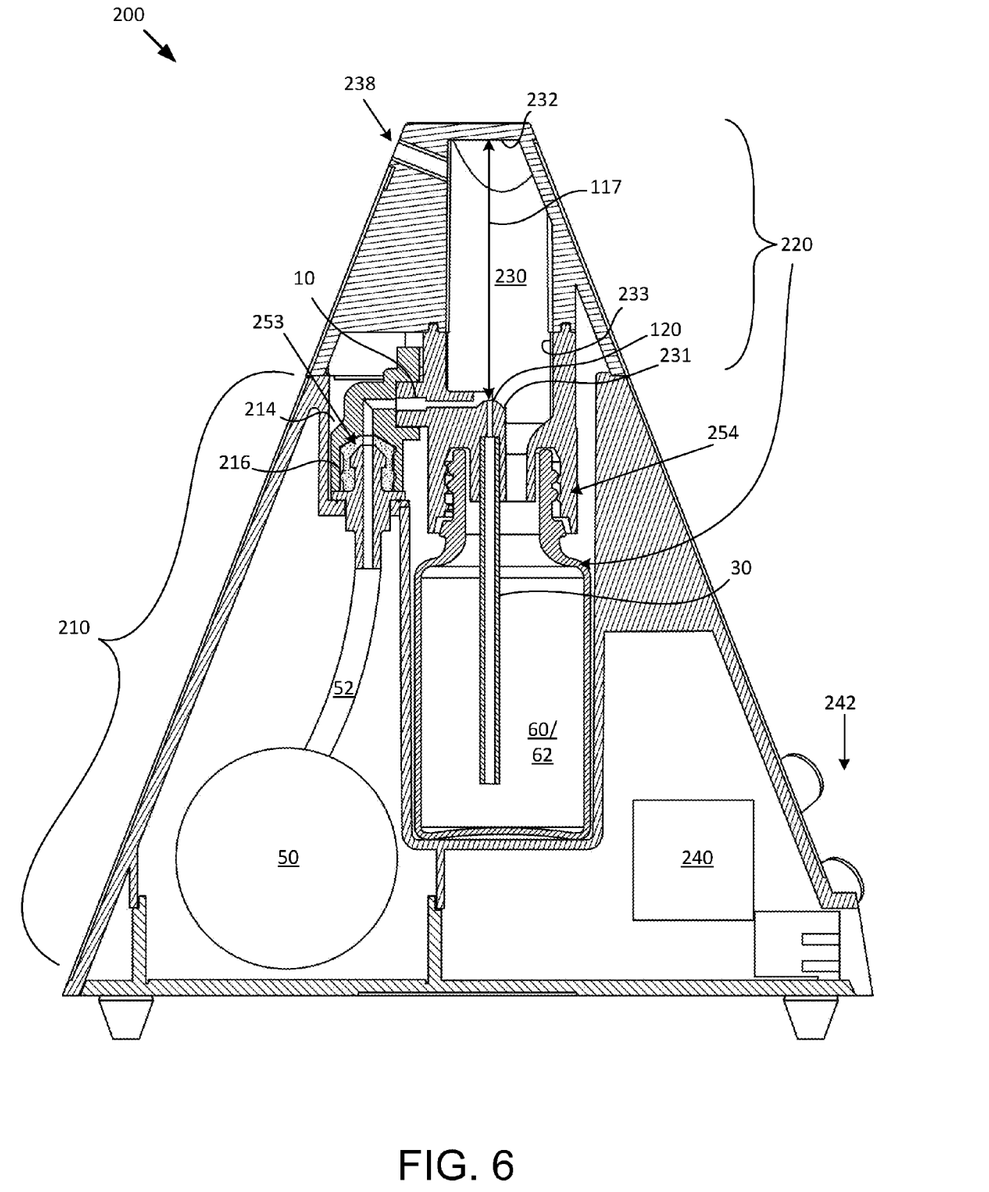

FIG. 6 is a cross-sectional side view of a diffuser system 200, according to one embodiment. As depicted, the diffuser system 200 includes a removable component 220 in an engaged position with a base 210. The removable component 220 includes a vent 238 near the top of a diffuser chamber 230. In one embodiment, the diffuser chamber 230 is integrated within the removable component 220. In another embodiment, however, the diffuser chamber 230 may be integrated within the base 210. In yet another embodiment, sections of the diffuser chamber 230 may be integrated within both the removable component 220 and the base 210. In such an embodiment, the diffuser chamber 230 is formed when the removable component 220 is in a properly engaged position with respect to the base 210 to form the walls of the diffuser chamber 230.

According to one embodiment, the dome-shaped surface 120 is a protrusion of a first wall 231 of the diffuser chamber 230. As briefly described above, the diffuser chamber 230 may also have a second wall 232, opposite the first wall 231, displaced a distance (second distance 117) from the first wall 231. According to one embodiment, the second distance 117 is large enough so as to not substantially increase the operable velocity of the gas stream across the dome-shaped surface 120. A third wall 233 of the diffuser chamber 230, although described in greater detail below with reference to FIG. 7, may be positioned in downstream combination stream 136 receiving communication from the injection port 110 and the dome-shaped surface 120.

The liquid vial 62 in the depicted embodiment is detachably coupled to the removable component 230. As described above, the liquid vial 62 may contain a liquid to be diffused into the atmosphere through the vent 238. In one embodiment, the removable component 220 includes a vial coupling mechanism 254 that facilitates the detachable coupling between the removable component 220 and the liquid vial 62. For example, the vial coupling mechanism 254 may include a threaded member that interacts with a standard essential oils vial, according to one embodiment. In another embodiment, the vial coupling mechanism 254 may include spring-loaded clips, straps, ties, fasteners, etc.

The removable component 220 may also include a first gas coupling mechanism 253 for detachably coupling the gas supply line 10 to the pressurized gas source 50 via the pressurized gas channel 52. The first gas coupling mechanism 253 may be a rubber gasket (as shown), one or more O-rings, or another suitable structure configured to make a substantially air-tight seal between pressurized gas channel 52 and the second gas coupling mechanism 216 of the gas supply line 10. As shown, the second gas coupling mechanism 216 can be shaped and sized or otherwise configured to selectively fit over the first gas coupling mechanism 253. In this position (as shown), the second gas coupling mechanism 216 can connect to and/or couple with the first gas coupling mechanism 253 to make a substantially air tight seal. Gas may then flow from the pressurized gas source 50 through the pressurized gas channel 52 the connected first gas coupling mechanism 253 to the gas supply line 10. As shown, in some embodiments, the second gas coupling mechanism 216 can be a female coupling mechanism having an internal cavity configured to selectively receive the first gas coupling mechanism 253, which can be a male coupling mechanism. When joined, the two coupling mechanisms can form a press fit, air-tight connection. In other embodiments, the second gas coupling mechanism 216 may be a male coupling mechanism and the first gas coupling mechanism 253 may be female coupling mechanism. In still other embodiments, these two parts may have other shapes, sizes, and configurations that permit a substantially air-tight seal therebetween when they are selectively coupled.

Conveniently, as shown, the first gas coupling mechanism 253 and the second gas coupling mechanism 216 may be selectively coupled and decoupled by the mere action of joining and separating, respectively, the removable component 220 from the body 210 of the diffuser system 200. In some embodiments, one or more securing mechanism 222, such as a magnet, may secure the removable component 220 in place on the body 210 to ensure a complete connection of the first gas coupling mechanism 253 and the second gas coupling mechanism 216. Additionally or alternatively, the weight of the removable component 220 and the liquid source 60 can provide the downward force necessary to completely couple the first gas coupling mechanism 253 and the second gas coupling mechanism 216.

The removable component 220, according to one embodiment, includes a liquid supply line 30 that is fixed to the removable component 220 but that extends into the replaceable liquid vials 62 to draw up liquid particles (particle stream 134) when a suction force is generated by the diffuser apparatus 100. The liquid supply line 30 can be a flexible tube, rigid tube, or other suitable structure. The liquid supply line 30 may be configured to reach to the bottom of a liquid vial 62 attached to the removable component 220 so that it may access all of the liquid in the liquid vial 62.

Figure 7:
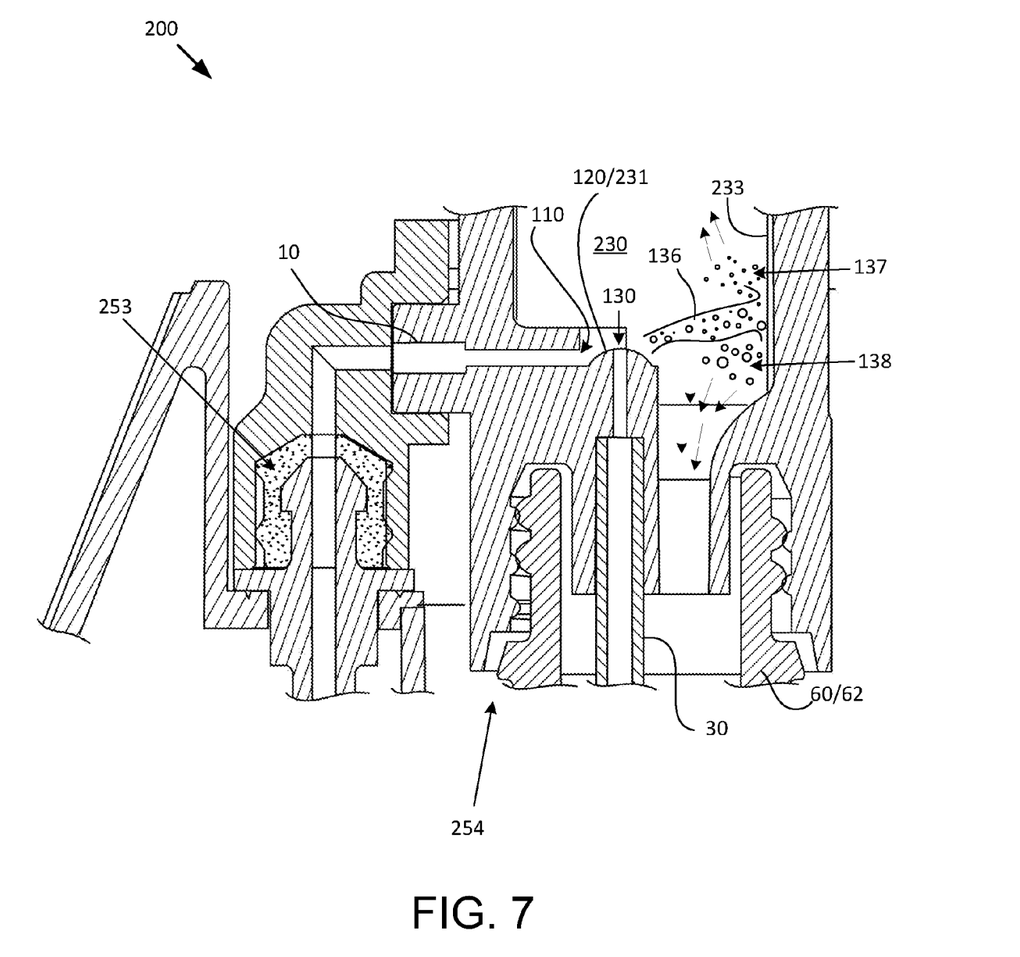

FIG. 7 is a magnified cross-sectional side view of the diffuser system 200 of FIG. 6, according to one embodiment. In order to avoid obscuring the depiction of the combination stream 136, the gas stream 118 and the particle stream 134 are not shown in FIG. 7. The combination stream 136 is a combination of the gas stream 118 emitted from the injection port 110 and the particle stream 134 drawn up through the suction port 130. Once again, the combination stream 136 is depicted with a plurality of circles of various sizes. These circles are not actual, physical representations of the size, dimensions, or concentration of the liquid particles drawn up from the liquid vial 62.

FIG. 7 shows the combination stream 136 contacting a third wall 233 of the diffuser chamber 230. Upon hitting the third wall 233, a heavy fraction 138 of the liquid particles may fall back down into the liquid vial 62 through an opening in the bottom of the diffuser chamber 230. A light fraction 137 of the liquid particles may diffuse towards the upper end of the diffuser chamber 230 and pass through the vent 238 (not depicted) and out into the atmosphere. As described above, the liquid vial 62 may contain certain liquids and/or oils that have a pleasant smell or that result in health and wellness benefits upon inhalation.

The described features, structures, advantages, and/or characteristics of the subject matter of the present disclosure may be combined in any suitable manner in one or more embodiments and/or implementations. In the above description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the above description and appended claims, or may be learned by the practice of the subject matter as set forth above.

In the above description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Numerical data may be expressed or presented herein in a range format. It is to be understood that such a range format is used merely for convenience and brevity and thus should be interpreted flexibly to include not only the numerical values explicitly recited as the limits of the range, but also as including all the individual numerical values or sub-ranges encompassed within that range as if each numerical value and sub-range is explicitly recited. As an illustration, a numerical range of "about 1 to 5" should be interpreted to include not only the explicitly recited values of about 1 to 5, but also include individual values and sub-ranges within the indicated range. Thus, included in this numerical range are individual values such as 2, 3, and 4 and sub-ranges such as 1-3, 2-4, and 3-5, etc. This same principle applies to ranges reciting only one numerical value and should apply regardless of the breadth of the range or the characteristics being described.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

The present subject matter may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A diffuser apparatus comprising:
    a gas supply line, connectable in gas receiving communication with a pressurized gas source, the gas supply line comprising an injection port facing a first direction, the injection port operably emitting a gas stream into a diffuser space in the first direction;
    a dome-shaped surface positioned a first distance away from the injection port in downstream fluid communication with the gas stream, wherein the gas stream is directed at a base portion of the dome-shaped surface; and
    a liquid feed line, connectable in fluid receiving communication with a liquid source, the liquid feed line com- 
prising a suction port disposed on a crest portion of the dome-shaped surface and facing a second direction, wherein the first direction and the second direction are not parallel, wherein a second distance between the dome-shaped surface and an element opposite the dome-shaped surface is greater than a diameter of the injection port so that no narrowing venturi-type effect occurs as the gas stream passes over the dome-shaped surface, wherein operably passing the gas stream over the suction port, by the Coanda effect, increases a velocity of the gas stream and suctions a particle stream through the liquid feed line to form a combination stream.

2. The apparatus of claim 1, wherein the diffuser space comprises a diffuser chamber and the dome-shaped surface comprises a protrusion on a first wall of the diffuser chamber.

3. The apparatus of claim 2, wherein a second wall of the diffuser chamber, opposite the first wall, is displaced the second distance from the dome-shaped surface.

4. The apparatus of claim 2, wherein a second wall of the diffuser chamber, opposite the first wall, is displaced the second distance from the dome-shaped surface so that the second distance is greater than a diameter of the injection port.

5. The apparatus of claim 1, wherein the first direction is substantially perpendicular to the second direction.

6. A diffuser apparatus comprising:

a removable component detachably engageable with a base, the removable component comprising a liquid source; and a diffuser chamber at least partially integrated with the removable component, the diffuser chamber comprising:

an injection port in fluid receiving communication with a pressurized gas channel of the base, the injection port operably emitting a gas stream into the diffuser chamber, a dome-shaped surface protruding from a first wall of the diffuser chamber, the dome-shaped surface positioned a first distance away from the injection port in downstream fluid communication with the gas stream, wherein the gas stream is directed at a base portion of the dome-shaped surface, and a suction port disposed on a crest portion of the dome-shaped surface, the suction port in fluid receiving communication with the liquid source, wherein a second distance between the dome-shaped surface and a second wall of the diffuser chamber, opposite the first wall, is greater than a diameter of the injection port so that no narrowing venturi-type effect occurs, wherein operably passing the gas stream over the suction port, by the Coanda effect, increases a velocity of the gas stream and suctions a particle stream from the liquid source into the diffuser chamber to form a combination stream.

7. The system of claim 6, wherein the liquid source comprises a liquid vial coupled to the removable component and at least a portion of the diffuser chamber is positioned above and open to at least a portion of the liquid vial.

8. The system of claim 7, wherein the combination stream operably contacts a third wall of the diffuser chamber and a heavy fraction of the combination stream falls into the liquid vial and a light fraction of the combination stream passes through a vent.

9. The system of claim 6, further comprising a securing mechanism for securing together the base and the removable component.

10. The system of claim 6, wherein the liquid source comprises a liquid vial detachably coupled to the removable component such that the liquid vial is replaceable.

11. The system of claim 6, wherein the injection port is in fluid receiving communication with the pressurized gas channel of the base via a gas coupling mechanism.

12. The system of claim 11, wherein the gas coupling mechanism includes a gasket.

13. The system of claim 6, wherein the base comprises a pressurized gas source in fluid communication with the pressurized gas channel.

14. The system of claim 6, further comprising a controller integrated with the base for controlling dynamics of the gas stream.

15. The system of claim 14, wherein the base further comprises a user interface for regulating the controller.

* * * * *